United States Patent [19]
Malke et al.

[11] Patent Number: 5,187,098
[45] Date of Patent: Feb. 16, 1993

[54] DNA ENCODING HYBRID STREPTOKINASES WITH PLASMINOGEN FIBRIN BINDING DOMAINS

[75] Inventors: Horst Malke, Jena-Lobeda, German Democratic Rep.; Joseph J. Ferretti, Oklahoma City, Okla.

[73] Assignee: Board of Regents of the University of Oklahoma, Norman, Okla.

[21] Appl. No.: 888,420

[22] Filed: May 22, 1992

Related U.S. Application Data

[63] Continuation of Ser. No. 348,206, May 9, 1989, abandoned, which is a continuation-in-part of Ser. No. 212,254, Jun. 27, 1988, Pat. No. 5,066,589, which is a continuation of Ser. No. 585,417, Mar. 2, 1984, Pat. No. 4,764,469.

[51] Int. Cl.⁵ .................. C12N 15/00; C12N 9/68; C12N 9/70; C12N 15/58
[52] U.S. Cl. .................. 435/320.1; 536/23.2; 536/23.4; 435/216; 435/217; 435/226
[58] Field of Search .................. 435/226, 240.2, 212, 435/217, 216, 320.1; 536/27

[56] References Cited

U.S. PATENT DOCUMENTS 4,764,469  8/1988  Ferretti et al. .................. 435/216

FOREIGN PATENT DOCUMENTS 293934  12/1988  European Pat. Off. .

OTHER PUBLICATIONS

Klessen, C. et al., *Mol. Gen. Genet.*, 212: 295-300, 1988.
Malke, H. et al., *PNAS*, 81: 3557-61, 1984.
Malke, H. et al., *Gene*, 34: 357-62, 1985.
Maniatis, T. et al., *Molecular Cloning: A Laboratory Manual*, Cold Spring Harbor, NY, pp. 1.7-1.8, 1982.
Forsgren et al., *FEBS Letters*, 213(2): 254-60, 1987.
Ahmed, *Gene*, 28: 37-43, 1984.

*Primary Examiner*—Garnette D. Draper
*Assistant Examiner*—Marianne Porta Allen
*Attorney, Agent, or Firm*—Dunlap, Codding & Lee

[57] ABSTRACT

Compositions and methods of the synthesis of hybrid streptokinase with fibrin binding domains based on gene fusion technology. Recombinant DNA methods have been used to fuse gene segments for streptokinase and for fibrin-binding domains and express the fused gene in prokaryotic microorganisms, and the respective expressed protein is subsequently obtained by biotechnologic fermentation for the purpose of use in clinical medicine.

6 Claims, No Drawings

DNA ENCODING HYBRID STREPTOKINASES WITH PLASMINOGEN FIBRIN BINDING DOMAINS

CROSS REFERENCE TO RELATED APPLICATIONS

This is a continuation of co-pending application U.S. Ser. No. 07/348,206 filed on May 9, 1989, entitled "HYBRID STREPTOKINASES WITH FIBRIN BINDING DOMAINS AND METHODS FOR THE SYNTHESIS OF SAME," now abandoned which is a continuation-in-part of U.S. Ser. No. 07/212,254 filed on Jun. 27, 1988, entitled "STREPTOKINASE CODING RECOMBINANT VECTORS," now U.S. Pat. No. 5,066,589, which is a continuation of U.S. Ser. No. 06/585,417 filed on Mar. 2, 1984, entitled "STREPTOKINASE CODING RECOMBINANT VECTORS," now U.S. Pat. No. 4,764,469.

U.S. Ser. No. 212,254 now U.S. Pat. No. 5,066,589, and U.S. Pat. No. 4,764,469, described above, are hereby incorporated by reference in this application.

DETAILED DESCRIPTION OF THE PREFERRED EMBODIMENTS

The present invention comprises a microbiologic-genetic method for the synthesis of hybrid streptokinases and hybrid streptokinases which possess fibrin binding domains. The goal was to produce by biotechnology the first streptokinases which possess thrombus (clot) selectivity. The technical approach to reach this goal is based on genetic technology, whereby prokaryotic organisms are transformed with expression plasmids, specifically with pKSK expression plasmids which carry DNA coding for the amino acid sequences of fusion proteins. The fusion proteins are composed of at least one fibrin-binding domain of human plasminogen as well as a functional component of the streptokinase molecule. Following cultivation of this recombinant prokaryotic strain, the gene product; i.e., the respective hybrid streptokinase, is isolated from the culture fluid. In a preferred way of solving the problem, trihybrid streptokinases are synthesized, in which the N-terminus is the N-terminal hexapeptide of beta-galactosidase, the central portion is the Kringle domain(s) of human plasminogen, and the C-terminal region is the streptokinase of Streptococcus equisimilis H46A. With this method, using the direct coding synthesis, hybrid streptokinases are produced which possess thrombus (clot) selectivity, and a clinically desirable property is obtained.

Kringle Streptolinase

Streptokinase (generic abbreviation: SK) is one of the most frequently used fibrinolytic agents in clinical medicine. As a distinct gene product of pathogenic organisms it is a possible virulence factor of bacteria, and the clinical material obtained specifically binds with plasminogen (abbreviation: Pg) of blood plasma and forms a SK-Pg complex, which transforms free plasminogen to the enzymatically active plasmin. Plasmin functions as a serine protease by limited proteolysis of the fibrin network of blood clots. This reaction of Pg-activation is the basis of action of SK in the fibrinolytic therapy for the disintegration of the fibrin network which is the main component of occluded vessels such as in thromboembolisms (namely, myocardial infarcts, deep vein thrombosis, lung embolisms, peripheral arterial thrombosis, etc.).

Streptokinase formation occurs in a large number of different pathogenic streptococcal species of serologic groups (group A, C, G etc.). The different streptokinases are not identical with regard to their primary structures, as has been shown in recent reports of molecular epidemiology studies (Huang, T. T., H, Malke, and J. J. J. Ferretti. 1989. Infect. Immun. 57:502–506) and nucleotide sequence analysis of their genes (Huang, T. T., H. Malke, and J. J. Ferretti, 1989. Molec. Microbiol. 3:197–205; Walter, F., M. Siegel, and H. Malke, 1989a. Nucl. Acids Res. 17:1262; 1989b, Nucl. Acids Res. 17:1261).

For streptokinase production in the pharmaceutical industry the group C Streptococcus equisimilis strain is exclusively used, which has the characteristics described by Christensen of strain H46A. In each case the streptokinase produced by Kabi (Sweden) and of the pharmaceutical combine GERMED (Arzneimittelwerk, Dresden, DDR) under the trade names Kabikinase and Awelysin, respectively, seem to be structurally identical to the protein produced by strain H46A (Malke, H., B. Roe, and J. J. Ferretti, 1985. Gene 34: 357–362). Following the cloning and sequence analysis of the streptokinase gene (skc) of strain H46A (Malke, H., and J. J. Ferretti, 1984. Proc. Nat'l. Acad. Sci. USA 81:3557–3561; Malke, H., B. Roe, and J. J. Ferretti, 1985. Gene 34: 357–362) recombinant vectors with the skc gene construct carried in host organisms, which originally did not produce Skc (abbreviation for the streptokinase protein specified by the skc gene) were constructed and are described in (U.S. Pat. Nos. 4,764,469, DD 249 037, DD 250 546). With Skc production by heterologous hosts, it is now much easier to experimentally influence, by genetic and molecular means, an increase of the Skc synthetic capacity by gene dosage effects and regulatory mechanisms of product synthesis. By the selection of appropriate host organisms one can now use non-pathogenic host organisms for Skc production, with no accompanying toxic products produced and thereby simplify the down stream processing. Thus, manufactured recombinant Skc is in the pharmacologic sense not a new product, but merely the same known product, which is now profitable to produce.

The ideal goal of thrombolytic therapy is the specific activation of fibrin bound plasminogen and its subsequent lysis in vessels. This ideal does not, on the surface, appear to be obtainable with streptokinase or with recombinant streptokinase because the proteins additionally activate circulating plasminogen and lead to proteolysis of fibrinogen, coagulation factors, and of components of the complement system. The reduced concentration of clot factors and of fibrinogen as well as the inhibitory effect of fibrin degradation products on blood platelet aggregation and fibrin polymerization leads to a potential dangerous hemostatic defect (hemorrhage).

In order to limit the systemic activation of plasminogen, the Beecham Group (since 1979) has developed PLC stable derivatives of the SK-Pg complex in which the active serine of the Pg component is blocked by acylation (Patent No. EP 0 009 879, EP 0 028 489, EP 0 091 240, EP 152 736, US 4 597 283). These so-called APSAC substances (trade name: Eminase) have fibrin affinity that is characterized by the presence of plasminogen kringles, do not react with circulating Pg or alpha 2 antiplasmin, and only become active after dissociation of the acyl group (deacylation). Thus far, however, convincing clinical data are missing which would show that APSAC substances are superior to the original streptokinase. In addition, the production requires the use of pure plasminogen for complex formation with streptokinase.

During the past few years, special vectors developed in basic research have been used more and more to fuse together, in the same reading frame, genes or gene segments of varying origin (cf for instance Silhavey, T. J., M. L. Berman, and L. W. Enquist, 1984. Experiments with Gene Fusions. Cold Spring Harbor Laboratory, Cold Spring Harbor, N. Y. ). Under certain conditions such genes code for hybrid proteins with mixed properties. The cloned skc gene also possesses sufficient capabilities and information to be used in gene fusion technology (Klessen, C., K. H. Schmidt, J. J. Ferretti, and H. Malke, 1988. Molec. Gen Genet. 212:295–300) and there are special vectors which make it possible to fuse any DNA with the skc gene which is blunted at the 5' end (so-called ORF vectors). These vectors, however, have not thus far been used for the fusion of skc with DNA which codes for fibrin-binding domains (fbd).

The present invention is based on the approach of genetic-microbiologic methods of gene fusion technology which describe functional segments of the streptokinase gene (skc) which are linked with functional segments of DNA encoding fibrin-binding domains; construction of new plasmid vectors which contain the fused nucleotide sequences; and microorganisms that can be used for the synthesis of such DNA encoded streptokinases.

According to the invention, this task is basically accomplished by using gene-fusion technology to initially construct expression plasmids, which carry the DNA coding for the amino acid sequences of fusion proteins, which include at least one fibrin-binding domain of human plasminogen as well as a functional component of the streptokinase molecule (abbreviated: fbd-'skc gene fusion). Using such fbd-'skc recombinant expression plasmids which have been introduced by transformation for the first time into prokaryotic recipients; i.e., including bacterial species as well as L-form species of bacterial origin, and afterward these transformed organisms are cultured. Finally, the hybrid streptokinase which was formed during fermentation by the individual variants of the experiment are isolated after cell lysis or from the culture medium, respectively.

The basics for this invention are further enhanced by the fact that for the transformation of a producer organism of the above mentioned characteristics, a fbd-'skc recombinant expression plasmid of the pKSK000 family is always constructed, which is a derivative of a polylinker containing plasmid and an open reading frame vector (abbreviation: ORF-vector) of the pKM series known in the literature, and capable of replication in gram-negative as well as gram-positive recipients. Preferably, such a pKM vector is used for the construction of a fbd-'skc recombinant expression plasmid, which contains (oriented in the 5' to 3' direction) recombined partial segments made up of the following sequence elements: prokaryotic expression or expression secretion units, respectively, which have a natural source of at least a translation initiation codon; polylinker or restriction sites, respectively; and a skc structural gene with a natural transcription and translation termination signal and coding for a N-terminal blunted streptokinase which retains the capacity for plasminogen (abbreviation: Pg) -activation, in an "out-of-frame" arrangement with respect to the translation initiation codon. The pKM vectors used specify a streptokinase-negative phenotype.

For the construction of a fbd-'skc recombinant expression plasmid of the pKSK family, a DNA fragment is used which codes for at least one fibrin-binding domain of the human plasminogen molecule, and is prepared with knowledge of the complete cDNA sequence of the Pg gene (published by Forsgren et al., FEBS Lett. 213:254, 1987) by use of a well known procedure for chemical synthesis or by isolation from a pg containing recombinant plasmid.

In basic research, it is known that the so-called "kringle" domains of Pg impart a fibrin-binding specificity to this blood protein. All in all, a total of 5 potential fibrin-bidding domains (abbreviation: Fbd) named kringles 1–5, have been located on the Pg molecule, and correspondingly on the 5 Fbd-coding regions (fbd) of the pg gene. Similarly, it is also known that the individual Fbds of Pg are not equivalent concerning the strength of their fibrin binding domains. For example, the kringle 1 domain of the Pg molecule imparts a greater magnitude of affinity for fibrin than each of the other four kringles.

Each DNA fragment, coding for at least one Pg-binding domain, was obtained either by chemical synthesis or by isolation from a pq recombinant carrier plasmid, and was inserted into the polylinker domain of the ORF-pKM vector so that the skc reading frame was restored. Once ligation was carried out in this fashion, a collection of fbd-'skc recombinant expression plasmids was obtained and given the designation, "expression plasmids of the pKSK000 family." These expression plasmids of the pKSK000 family are used for transformation of certain producer organisms from the above mentioned recipient collection. Depending on the pKM expression vector, which is referred to in the individual variants of this procedure, there are in the pKSK000 family of constructs the following: a) plasmids which replicate solely in gram negative bacteria as well as stable L-forms from which they originate; b) plasmids which replicate solely in gram-positive bacteria as well as stable L-forms from which they originate; and c) shuttle plasmids which can replicate in bacterial recipients or their L-forms of both main groups.

Furthermore, there are in the pKSK family of constructs, depending on the individually included pKSK expression vector, as the case may be plasmids in which the respectively created fbd-'skc gene fusion is elongated at the 5' end by several codons of the lacZ gene if needed, from which the *E. coli* lactose promoter-operator (abbreviation: lacPO) is controlled and plasmids in which the respectively created fbd-'skc gene fusions are elongated at the 5′ end by several codons of the streptococcal exotoxin type A from which *Streptococcus pyogenes* speA expression secretion is controlled.

The results of this work represent the procedural steps necessary for the construction of pKSK000 expression plasmids containing lacZ′-fbd-;skc and speA′-fbd-'skc recombinant gene fusions.

The collection of fbd-'skc recombinant expression plasmids is complemented by an additional variation of the submitted methodology by the partial family of *E. coli* pKSK000T expression plasmids. Each pKSK000T plasmid itself is a derivative of the polylinker-carrying expression vector of the pT7T3 series known from the literature. To accomplish this, the fbd-'skc fusion genes, i.e., the DNA components which encode the Pg-kringle structures, as well as the blunted streptokinase, are removed from the pKSK000 plasmids and are inserted into the polylinker of pT7T3, which in turn carries the ColE1 origin of replication. This subcloning is based on the findings that in the individual fbd-'skc gene fusions, as they were created in the course of the construction of the plasmids of the pKSK000 family and are now present in these plasmids, there are no SstI or SphI cleavage sites. In the resulting pKSK000T plasmids, the fbd-'skc gene fusions are elongated at the 5' end by several codons of the lacZ gene, and in each case are under expression control of the T7 promoter.

Among the pKSK000 and pKSK000T expression plasmids, respectively, which contain the first made fbd-'skc gene fusions, the submitted invention is further enhanced in its biotechnology sections as follows: for transformation with a lacZ'-fbd-'skc recombinant pKSK000 expression plasmid, ampicillin-resistant E. coli recipient strains are used. During the agar plate culture of ampicillin-resistant clones from such transformed cell populations, the synthesis of the gene product with Pg-activating capacity can be verified by zymography. Following cell growth, a trihybrid LacZ'-Fbd-'Skc fusion protein is isolated from the cells following their lysis.

For transformation with a speA'-fbd-'skc recombinant pKSK000 expression plasmid one uses a) chloramphenicol and/or erythromycin-sensitive E. coli recipient strains, respectively; b) erythromycin-sensitive *Streptococcus sanquis. Streptococcus lactis,* or *Bacillus subtilis* recipients, respectively; or c) erythromycin and/or chloramphenicol-sensitive stable L forms of *Proteus mirabilis, E. coli. B. subtilis,* or *S. faecium* strains.

During the agar plate culture of chloramphenicol, erythromycin-resistant clones, respectively, from such transformed cell populations, the ability of clones to synthesize gene products with Pg-activating capacity is once again verified using zymography, and at the end of cell culture a new trihybrid SpeA'-Fbd-'Skc fusion protein is isolated via cell lysis (case a) or from the culture fluid (as in cases b and c). For the transformation with a lacZ'-fbd-'skc recombinant pKSK000T expression plasmid, ampicillin-sensitive *E. coli* recipient strains are used. Subsequently, *E.* coli strains which have been transformed with pKSK000T plasmids are transformed again with a second plasmid which encodes an inducible T7 RNA polymerase. During the agar plate culture of antibiotic-resistant clones from such transformed cell populations, synthesis of the gene products of Pg-activating capacity is verified if necessary by use of zymography, and at the end of cell culture, a trihybrid LacZ'-Fbd-'Skc fusion protein is isolated after cell lysis or from the culture fluid.

The PKM Vectors

In the preferred execution of the submitted invention, the following pKM vectors have been used as segments in the "Construction of fbd-'skc recombinant pKSK000 expression plasmids":

a) the ORF vector pKM2 (selective marker, ampicillin resistance); this plasmid vector which can replicate in *E. coli* carries a region with the sequence elements (in the 5' to 3' direction)

- *E. coli-lacPO* including codons for the 6 N-terminal amino acids of beta-galactosidase (abbreviation; lacZ'),
- *EcoRI-XbaI* partial polylinker of cloning vector pUC18 and
- a 1596 bp HincII fragment from chromosomal *Streptococcus equisimilis* H46A with the native transcription and translation termination signals, coding for a blunted streptokinase, which is missing in addition to the signal peptide, 13 N-terminal amino acids (abbreviation: 'skc gene), in an out-of-frame arrangement with respect to the translation initiation codon of the lacZ gene.

b) the ORF vector pKM3 (selective marker: ampicillin-resistance); this plasmid vector which also can replicate in *E. coli* carries a region with the sequence elements:

- *Streptococcus pyogenes*-soeA ESE including the codons for the 5 N-terminal amino acids of the mature streptococcal exotoxin type A (abbreviation; soeA'),
- modified SmaI-SalI partial polylinker of cloning vector pUC9, and
- a 1596 bp HincII fragment with the 'skc gene of the above mentioned out-of-frame arrangement to the translation initiation codon of the speA gene;

c) The ORF vector pKM5 (selective marker: chloramphenicol and erythromycin resistance); can replicate in *E. coli* as well as *Streptococcus* and *Bacillus,* carries the same sequence elements as pKM3.

Each of these three expression vectors determines a streptokinase -negative phenotype, since the 'skc, lacZ', and speA' gene segments, respectively, are in an out-of-frame position relative to each other, even though as is known through appropriate basic research, that the above mentioned 'skc gene contains the complete sequence coding for a functional Skc.

The Kringles

Furthermore, in the preferred method of implementation, one uses the recombinant plasmid pFDl, a derivative of the polylinker carrying *E. coli* cloning vector pUC18, which contains the complete cDNA for human plasminogen, as described in the literature and also as defined regarding the nucleotide sequence numbering (Forsgren et al., FEBS Lett. 213:254, 1987). For the procedurally correct construction of pKSK000 expression plasmids, the following are obtained from the carrier plasmid (pFD1) by initial digestion with the corresponding restriction enzymes:

a) a 502 bp PvuII-StuI fragment (nucleotide positions 196 to 697 of Pg-cDNA), which contains the complete cDNA for the Kringle 1 fibrin binding domain (abbreviation: Kl), as well as b) a 1014 bp HgiAI fragment (nucleotide positions 979 to 1992 of Pg cDNA), which contains the complete cDNA for the kringle 4 and 5 fibrin-binding domains. The above mentioned, Kl-coding Pg-cDNA fragment lies directly before the insertion in a ORF-vector of the pKM series which is already prepared.

The above mentioned HgiAI-Pg-cDNA fragment, which is an intermediate for several of the variants, is treated in a defined manner with Bal31 nuclease as well as Klenow enzyme, and a diverse mixture of cDNA subfragments are obtained, and each of these subfragments are then prepared for insertion into a known pKM vector.

In the first variant, in which the 1014 bp HgiAI fragment is treated in a defined manner with nuclease Bal31 as well as Klenow enzyme, one obtains a mixture of cDNA subfragments coding for K4+K5.

In a second variant, in which the 1014 bp fragment is treated in a defined manner with nuclease Bal31 and Klenow enzyme, one obtains a mixture of cDNA subfragments, which codes for parts of K4 and K5.

In a third variant, the 1014 bp HgiAI fragment of plasmid pFD1 is treated in a defined treatment with nuclease Bal31 and Klenow enzyme is then digested completely with the restriction enzyme PstI, which allows a joining of the ligation reaction in this modified intermediate step, and now obtains a mixture of cDNA subfragments of minimal length which codes for a complete K4.

For the preferred method of construction of pKSK000 expression plasmids in a further modification of the above mentioned intermediate step, one obtains a mixture of Pg-cDNA subfragments which code for the K1+K2+K3+K4 fibrin binding domains. For this step, the carrier plasmid pFD1 is first totally digested with the restriction enzyme AhaII (pFD1-DNA has in the K5 region of its cDNA insert a single recognition sequence for this enzyme). With the resulting AhaII digest a defined further treatment with nuclease Bal31 as well as Klenow enzyme is carried out. The resulting DNA product is then digested with the restriction enzyme PvuII, thereby obtaining a cleavage of the "AhaII-Bal31 DNA" at nucleotide position 196. The digestion product thus obtained is subsequently subjected to electrophoresis and from the gel mixture is isolated the K1+K2+K3+K4 coding subfragments.

The PKSK000 Family

In the preferred approach, the present invention is continued in such a way that each of the fbd-cDNA segments is used as a) the K1-coding 502 bp PvuII-StuI fragment, as well as b) the Bal31 and Klenow treated K4+K5 coding mixture of subfragments from the 1014 HgiAI fragment as well as c) the Bal31 and Klenow treated K5 coding mixture from the 1014 bp HgiAI fragment, as well as d) the Bal31 and Klenow and PstI treated K4 coding mixture of subfragments from the 1014 bp HgiAI fragment, as well as e) finally, the AhaII+Bal31+-Klenow+PvuII treated mixture of K1+K2+K3+K4 coding subfragments and these are inserted into the SmaI opened polylinker of the ORF vector pKM2. With the resulting ligation products, in each parallel step, the ampicillin-sensitive E. coli JM109 recipient strain is then transformed in order to obtain, by way of screening for simultaneously ampicillin-resistant and Skc-positive clones, the following initial collection:

a2) PKSK056(K1)
b2) pKSK036 (K4+K5)
c2) pKSK029 (K5)
d2) pKSK351 (K4)
e2) pKSK067 (K1+K2+K3+K4) (type 1)
e2.1) pKSK069, (K1+K2+K3+K4) (type 2) respectively, of the pKSK000 expression plasmids as well as to produce sufficient quantities of plasmid DNA for the characterization and further use of these new plasmids.

Five or the six above referenced plasmids, namely, pKSK056, pKSK036, PKSK029, pKSK351, and pKSK067, are deposited in the American Type Culture Collection, 12301 Parklawn Drive, Rockville, Md. 20852 U.S.A. The referenced plasmids were deposited on May 14, 1992.

Plasmid pKSK056 is deposited under ATCC 68981. Plasmid pKSK056 contains a DNA sequence encoding the first part of a fusion protein, namely, human plasminogen fibrin binding regions (kringle 10, and a DNA sequence encoding the second part of a fusion protein, namely, the DNA sequence encoding streptokinase derived from Streptococcus equisimilis.

Plasmid pKSK036 is deposited under ATCC 68980. Plasmid pKSK036 contains a DNA sequence encoding the first part of a fusion protein, namely, human plasminogen fibrin binding regions (kringle 4 and kringle 5), and a DNA sequence encoding the second part of a fusion protein, namely, the DNA sequence encoding streptokinase derived from Streptococcus equisimilis)

Plasmid pKSK029 is deposited under ATCC 68983. Plasmid pKSK029 contains a DNA sequence encoding the first part of a fusion protein, namely, human plasminogen fibrin binding regions (kringle 5), and a DNA sequence encoding the second part of a fusion protein, namely, the DNA sequence encoding streptokinase derived from Streptococcus equisimilis.

Plasmid pKSK351 is deposited under ATCC 68982. Plasmid pKSK351 contains a DNA sequence encoding the first part of a fusion protein, namely, human plasminogen fibrin binding regions (kringle 4), and a DNA sequence encoding the second part of a fusion protein, namely, the DNA sequence encoding streptokinase derived from Streptococcus equisimilis.

Plasmid pKSK067 is deposited under ATCC 68984. Plasmid pKSK067 contains a DNA sequence encoding the first part of a fusion protein, namely, human plasminogen fibrin binding regions (kringle 1 and kringle 2 and kringle 3 and kringle 4), and a DNA sequence encoding the second part of a fusion protein, namely, the DNA sequence encoding streptokinase derived from Streptococcus equisimilis.

This method is based on the facts that follow. The above mentioned under a1) known K1 coding, 502 bp PvuII-StuI- cDNA fragment as well as at least always one subfragment in the fbd-cDNA mixtures mentioned under b1) to e1) represent an open-reading-frame (ORF). These sequences are next inserted by a ligation step according to the standard technique into vector pKM2 between lacPO and 'skc so that the 'skc reading frame is restored; i.e., an insertion activation of 'skc is achieved in each case. Each of the pKSK000 expression plasmids listed under a2) through e2.1) thus carries a functional lacZ'-fbd-'skc gene fusion. At the level of protein expression of such a "fused" gene which results in the formation of a fusion streptokinase consisting of three components to make the trihybrid streptokinase, and in each case the biological activity can be demonstrated by zymographic methods. Clones which synthesize such active trihybrid streptokinases are readily recognized in the primary transformation agar plates by caseinolytic or fibrinolytic zones around the colony after an overlay of assay medium which contains human plasminogen, and a substrate for activated plasminogen, such as casein or fibrin. In this connection, it is remarkable that the technique described above can be used to prove that synthesis of Lac'-Fbd-'Skc fusion proteins and with that functioning of the constructed lacZ'-fbd-'skc recombinant expression plasmids can be used in the E. coli transformation system, even though an optimal excretion of the respective heterologous gene product in the culture medium is not a given.

In a subsequent variation of the preferred technique, described under number a2) to e2.1) in which the designated expression plasmids are used to insert the respective fbd-cDNA fragments into the polylinker of the ORF-vector pKM5. Utilizing the ligation products thus produced, the erythromycin-sensitive *Streptococcus sanquis* Challis-6 recipient strain is transformed during each parallel step; and with the use of the screening procedure described previously, the following secondary collection a2) pKSK156 (K1)
b2) pKSK136 (K4+K5)
c2) pKSK129 (K5)
d2) pKSK451 (K4)
e2) pKSK167 (K1+K2+K3+K4) (type 1)
e2 1) pKSK169, (K1+K2+K3+K4) (type 2) respectively, is obtained from the now speA'-fbd-'skc recombinant pKSK000 expression plasmid, which at the same time can verify the biological activity as already mentioned and the functionability of these constructs.

The PKSK000T Family

In a last variant of the preferred method of execution, the fbd- 'skc gene fusion is taken in the form of a cassette from one of two available collections of pKSK000 expression plasmids, namely from:

a1) pKSK056 (K1) and pKSK156 (K1)
b1) pKSK036 (K4+K5) and pKSK136 (K4+K5)
c1) pKSK029 (K5) and pKSK129 (K5)
d1) pKSK351 (K4) and pKSK451 (K4)
e1) pKSK067 (K1+K2+K3+K4) (type 1) and pKSK167 (K1+K2+K3+K4) (type 1)
e1.1) pKSK069 (K1+K2+K3+K4) (type 2) and pKSK169, (K1+K2+K3+K4) (type 2) respectively, in the form of SstI-SohI fragments and are inserted into the polylinker of the *E. coli* expression vector pT7T318U. Using the resulting ligation product, the ampicillin-sensitive *E. coli* strain JM109 is transformed. After a secondary transformation with the *E. coli* plasmid pGP1-2, which codes for an inducible T7-RNA polymerase, the following third collection a2) pKSK056T
b2) pKSK036T
c2) pKSK029T
d2) pKSK351T
e2) pKSK067T
e2.1) pKSK069T, respectively, of pKSK000T expression plasmids with functioning fbd-cDNA gene fusions are obtained by means of a screening procedure which follows the previously described pattern.

As can be ascertained from the above description, there exist in the mixture under e1) of fbd-cDNA subfragments, at least two individual K1+K2+K3+K4 coding fragments of varying length which in each case represent an open reading frame.

The Nucleotide Sequence of the PKSK000 Family

In connection with the production of pKSK000 and pKSK000T expression plasmids, respectively, recombinant clones which synthesize functionally active fusion streptokinases are further examined for the respective trihybrid streptokinase coding DNA. For this purpose, the corresponding recombinant DNA segment from selected expression plasmids which were produced according to appropriate techniques in sequence vectors as published in the literature are recloned and resequenced in the usual manner.

Based on the nucleotide sequences that are found, the junction points of the various components of fused DNA are ascertained; at the same time the correct reading frame links are verified.

Using this experimental procedure, for instance, it could be demonstrated that the expression plasmid pKSK056 carries a gene fusion coding for a Kringle (K1) streptokinase of the primary structure

```
     0    1        6 (1)      (4) 41     207 (5)     (10) 14      414
     ATG ACC ... TCG agc ... ccc CTG ... CAG Ggg ... gtc AAC ... AAA TAA
```

[0–6, lacZ codons; (1)–(4), polylinker codons; 41–207, plasminogen-cDNA codons; (5)–(10), polylinker codons; 14–414, 'skc codons]which specifies a trihybrid streptokinase composed of 585 amino acid residues (abbreviation K1 streptokinase pKSK056); the expression plasmid pKSK036 carries a gene fusion coding for a Kringle (K4+K5) streptokinase of the primary structure

```
     0    1        6 (1)      (4) 332    613 (5)     (10) 14      414
     ATG ACC ... TCG agc ... ccc GCC ... TCC Cgg ... gtc AAC ... AAA TAA
```

[0–6, lacZ codons; (1)–(4), polylinker codons: 332–613, plasminogen-cDNA codons; (5)–(10), polylinker codons; 14–414, 'skc codons]which specifies a trihybrid streptokinase composed of 700 amino acid residues (abbreviation: K4+K5-streptokinase pKSK036); the expression plasmid pKSK029 carries a gene fusion coding for a Kringle (K5) streptokinase of the primary structure

```
     0    1        6 (1)      (4) 420    612 (5)     (10) 14      414
     ATG ACC ... TCG agc ... ccc GGC ... TGG Cgg ... gtc AAC ... AAA TAA
```

[0–6, lacZ' condons; (1)–(4), polylinker condons; 420–612, plasminogen-cDNA condons; (5)–(10), polylinker condons; 14–414, 'skc condons] which specifies a trihybrid streptokinase composed of 611 amino acid residues (abbreviation K5-streptokinase pKSK029); the expression plasmid pKSK351 carries a gene fusion coding for a Kringle (K4) streptokinase of the primary structure

```
     0    1        6 (1)      (4) 316    507 (5)     (10) 14      414
     ATG ACC ... TCG agc ... ccc GGC ... TGG Cgg ... gtc AAC ... AAA TAA
```

[0–6, lacZ'codons; (1)–(4), polylinker codons; 316–507, plasminogen-cDNA codons; (5)–(10), polylinker codons; 14–414, 'skc condons] which specifies a trihybrid streptokinase composed of 610 amino acid residues (abbreviation K4-streptokinase pKSK351); the expression plasmid pKSK067 carries a gene fusion coding for a Kringle (K1+K2+K3+K4) streptokinase of the primary structure

```
   0  1     6 (1)    (4) 41     490 (5)     (10) 14    414
  ATG ACC...TCG agc...ccc CTG...CGA Ggg...gtc AAC...AAA TAA
```

[0–6, lacZ codons; (1)–(4), polylinker condons; 41–490, plasminogen-cDNA codons; (5)–(10), polylinker codons; 14–414, 'skc codons] which specifies a trihybrid streptokinase composed of 868 amino acid residues (abbreviation K1+K2+K3+K4-streptokinase pKSK067); and the expression plasmid pKSK069 carries a gene fusion coding for a Kringle (K1+K2+K3+ , ...reptokinase of the primary structure

```
   0  1     6 (1)    (4) 41     496 (5)     (10) 14    414
  ATG ACC...TCG agc...ccc CTG...ACT Ggg...gtc AAC...AAA TAA
```

[0–6, lacZ codons; (1)–(4), polylinker codons; 420–612, plasminogen-cDNA codons; (5)–(10), polylinker codons; 14–414, 'skc codons]which specifies a trihybrid streptokinase composed of 874 amino acid residues (abbreviation K1+K2+K3+K4-streptokinase pKSK069).

The Producer Microorganisms

The following are used as the producer strains for the trihybrid streptokinases which were constructed according to the standard methodology in the preferred construction a) in the case of lacZ'-fbd-'skc recombinant pKSK000 expression plasmids of the ampicillin-sensitive bacterial strain E. coli JM109;

b) in the case of the speA'-fbd-'skc recombinant pKSK000 expression plasmid of the erythromycin-sensitive bacterial strain Streptococcus sanguis Challis-6 as well as the erythromycin and chloramphenicol-sensitive stable L form strain Proteus mirabilis LVI, as well as, c) in the case of lacZ'-fbd-'skc recombinant pKSK000T expression plasmids of the ampicillin-sensitive bacterial strain E. coli JM109.

The agar plate culture of the recombinant microorganisms obtained in this manner; i.e., the E. coli JM109 (pKSK000) strains JM109(pKSK056),
JM109(pKSK036),
JM109(pKSK029),
JM109(pKSK351),
JM109(pKSK067),
JM109(pKSK069), respectively, the Streptococcus sanquis strains
Challis 6(pKSK156),
Challis 6(pKSK136),
Challis 6(pKSK129),
Challis 6(pKSK451),
Challis 6(pKSK167),
Challis 6(pKSK169), respectively, as well as finally, the E. coli strains
JM109(pKSK056T;pGP1-2),
JM109(pKSK036T;pGP1-2),
JM109(pKSK029T;pGP1-2),
JM109(pKSK351T;pGP1-2),
JM109(pKSK067T;pGP1-2),
JM109(pKSK069T;pGP1-2), are carried out in each case under the well known standard condition. In the case of the use of the collection of pKSK000T expression plasmids which, the following additional regimen (as has been designated above according to the resulting recombinant microorganism strains): for secondary transformation of the E. coli JM109(pKSK000T) intermediate strains, the vector pGP1-2 is used which encodes an inducible T7 RNA polymerase; rifampicin is added to the culture medium in the usual manner (for selective inhibition of the host RNA polymerase).

With the combination of both succeeding steps, the cultivation of the named E. coli JM109(pKSK000T;pGP1-2) strains, used the specificity of the T7 RNA polymerase at its own promoter, and proceeded with the exclusive expression of Kringle streptokinase.

For the aerobic agar plate fermentation in the preferred execution of the collection of recombinant producer organisms obtained from the invention; i.e., the above mentioned E coli JM109(pKSK000) strains,
S. sanquis Challis 6(pKSK000) strains,
P. mirabilis LVI(pKSK000) strains,
E. coli JM109(pKSK000T;pGP1-2) strains;

are used in the known bacteriological culture media. Depending on the specific combination of expression plasmid and recipient strains which are utilized in the respective recombinant prokaryotic producer organisms, and thereby are dependent on the design of the expression plasmids that were used, there occurs a cytoplasmic, periplasmic, or extracellular localization of the synthesized gene product, from which the formed trihybrid streptokinases are isolated. This occurs with inclusion of the following purification steps, partly by cell lysis (as in the case of all the E. coli JM109 strains) and partly from the culture fluid (as in the case of the recombinant S. sanguis Challis 6 as well as P. mirabilis strains).

For subsequent purifications, methods of molecular-sieving and ion exchange chromatography are used as the first substep. The final purification is accomplished by using affinity chromatography with lysine Sepharose or anti-plasminogen coupled Sepharose for Kringle domains, and/or octyl-sepharose for streptokinase. The purity of the resulting end product is verified through sodium dodecyl sulfate-polyacrylamide gel electrophoresis (SDS-PAGE).

The hybrid streptokinases which have been obtained according to the standard synthesis and workup are identified and characterized using gel electrophoresis, zymographic, and immunologic methods. Initially, the SDS-PAGE of the extracellular or periplasmic product material is performed; in this case, deviating from the normal preparation of the sample, no heat denaturation is included. Subsequently, zymography of the gels as described above in the already characterized streptokinase assay medium is undertaken. The fibrin-binding domains of the Kringle streptokinase are demonstrated by using Western Immunoblotting of the gels with application of a monospecific polyclonal or monoclonal antibody, which is directed to the fibrin-binding components of the hybrid streptokinase. In this method, the use of a polyclonal rabbit antiserum against human plasminogen which has been purified by immunoaffinity is preferred.

The advantages of the described invention are seen as follows: by means of the present methodology, hybrid streptokinases possessing clinically significant properties have been produced for the first time. For the biosynthesis of the hybrid streptokinases, prokaryotic producer organisms, among them L-form strains, are transformed with the expression plasmids containing the genes for the hybrid streptokinases. The expression plasmids are characterized on the basis of gene fusion technology and were constructed using a gene region coding for a functionally intact group C streptokinase as well as selected regions of sequences coding for fibrin-binding domains of human plasminogen. The hybrid streptokinases which have been synthesized according to the standard method are distinguished by their thrombus (clot) selectivity. In order to obtain the streptokinase molecules which have this intended additional property, it is not necessary in this technology or by these methods to resort to the protein chemistry methods of coupling streptokinase to plasminogen. Rather, the result obtained here is a direct microbiological coding synthesis of the desired hybrid streptokinases.

Based on a series of already well known methods of DNA isolation, the DNA synthesis and the DNA fusion is made possible by the genetic technological steps of this methodological solution, applied in several ways, towards the goal of an oriented design for diverse molecular forms of kringle-streptokinases.

The following examples illustrate the practice of the present invention:

EXAMPLES

Example 1

1.1) Preparation of the gene fusion vector pKM2 for the insertion of fbd DNA.

One ml of an overnight culture (ca. $3 \times 10^9$ cells) of strain E. coli JM109(pKM2) [deposited in the Depository for Microorganisms of the DDR, Zentralinstitut fur Mikrobiologie und experimentelle Therapie der Akadamie der Wissenschaften, Beutenbergstrasse 11, Jena, DDR-6900, under the register Nr. IMET 11361, and deposited in the American Type Culture Collection 12301 Parklawn Drive Rockville, Md. 20852, ATCC Designation #67964, on May 10, 1989.], is incubated in LB medium (per liter; Bacto-Tryptone 10 g, Bacto Yeast Extract, 5 g; NaCl, 10 g; pH 7.5) in the presence of 0.1 g/ml ampicillin in a 500 ml culture flask and shaken at 37° C. until the culture reaches the late logarithmic phase of growth. The cells are sedimented by centrifugation, washed, and lysed according to the alkali method (0.2N NaOH, 1% SDS) and after the addition of 15 volume equivalents of a potassium acetate solution (5M, pH 4.8) the chromosomal DNA is separated from the other cell components by centrifugation (20,000 rpm, 20 minutes, 4° C.). The fraction containing the plasmid DNA is mixed with 0.6 volumes of isopropanol and centrifuged for 30 minutes at 12,000 x g at room temperature to obtain the pKM2 DNA. The precipitate which has been obtained is washed with 70% ethanol and is dissolved in 8 ml TE buffer (10mM Tris-HCl, pH 8.0; 1mM EDTA) and to obtain purified pKM2 DNA, is subjected to ethidium bromide (Etbr.)-CsCl density centrifugation (45,000 rpm, 36 hrs.). The plasmid DNA, which has had the Etbr extracted from it, is dialyzed and stored in a concentration of 0.5 mg/ml-1.0 mg/ml TE at 4 C. To 89 ul of pKM2 DNA are added 10 ul SmaI buffer, 1 ul DTT solution (100 mM) and 100 units of SmaI enzyme. The mixture is incubated for 2 hours at 33° C. and the cleaved DNA is subjected to phenol extraction, ethanol precipitation, and is dissolved in 50 ul of TE buffer. The 4282 base pair (bp) pKM2 vector DNA fragment which has been linearized and prepared for DNA insertion is stored at −20° C.

1.2) preparation of fbd DNA.

Preparation of the cDNA plasmid insert of human plasminogen.

The complete cDNA for human plasminogen, as it is defined in the literature pertaining to nucleotide sequence as well as base numbering (Forsgren et al., FEBS Lett. 213:254, 1987) is isolated primarily in the form of the recombinant E. coli plasmid pFD1 under conditions as described in 1.1).

Isolation of fbd DNA which codes for plasminogen kringle 1 (K1).

pFD1 DNA (24 ul at approximately 1 ug/ul) is cleaved sequentially with 20 U each of PvuII and StuI. After electrophoresis of the DNA digestion mixture in LMP agarose (1%), the 502 bp PvuII-StuI fragment (nucleotide positions 196-697 of the cDNA for plasminogen which codes for K1 is isolated from the gel, purified by phenol extraction, ethanol precipitated and dissolved in 15 ul of TE buffer. This fragment can be used without any further digestion for insertion into the SmaI cleaved pKM2 DNA and results in the complete restoration of the 'skc reading frame.

Preparation of fbd DNA coding for plasminogen kringle 4 (K4).

pFD1 DNA (50 ul at approximately 1 ug/ul) is completely digested with 20 U HgiAI. Following electrophoresis of the digest in LMP agarose (0.8%) the 1014 bp HgiAI fragment (nucleotide positions 979-1992) which codes for K4 plus K5, is isolated from the gel, purified by phenol extraction and ethanol precipitated, and is dissolved in 50 ul of TE buffer. 24 ul of the HgiAI fragment solution is digested exonucleolytically with 5 U Bal31 at room temperature for 10 seconds, and 1, 2, 3, 4, and 5 minutes, respectively. The Bal31 digestion is terminated with phenol and subsequently the digestion mixtures are purified after phenol extraction and ethanol precipitation. The purified Bal31 digestion mixtures are treated in "aliquote" amounts of 10 ul for the repair of DNA ends, in the presence of the four desoxynucleotide triphosphates and Klenow enzyme (1U) for 30 minutes at room temperature, followed by treatment at 70° C. for 10 minutes and stored at −20° C. until further use.

Preparation of fbd DNA which codes for plasminogen kringle 4 and 5 (K4+K5).

A mixture of fbd DNA subfragments which code for K4+K5 is prepared with some modification according to the procedure described above. This is accomplished by Bal31 digestion with 5 U of enzyme under the same conditions for 10, 20, 30, 40, 50, and 60 seconds.

Preparation of fbd DNA coding for a minimal length kringle 4 (K4) of human plasminogen.

The 1014 bp HgiAI fragment (see above) contains an internal PstI site which lies in the sequence coding for K4. Bal31 digestion of this HgiAI fragment and subsequent PstI digestion and then ligation, under standard conditions, results in recombination in such a way that K4-coding fragments of minimal length (approximately 300 bp) are obtained.

Preparation of fbd DNA coding fragments of human plasminogen that code for kringle 1 through 4 (K1+K2+K3+K4).

pFD1 DNA (32 ul of approximately 1 ug/ul) which contains a single AhaII site in the K5 region of the cDNA insert (nucleotide position 1573) is digested completely with 12 U of AhaII The total AhaII digest is further digested for 1 minute at room temperature with 0.7 U Bal31 and subsequently purified by phenol extraction and ethanol precipitation. The purified Bal31 digest is subjected, as above, to the end filling reaction with Klenow enzyme, is purified by phenol extraction and ethanol precipitation, and then dissolved in 32 ul of TE buffer. This DNA preparation is digested with 20 U PvuII in order to obtain a cleavage of "AhaII-Bal31" DNA at nucleotide position 196. The entire PvuII digestion product is subjected to agarose gel electrophoresis and a DNA mixture which migrated in the range of 1300 to 1380 bp is isolated from the gel and, after phenol extraction and ethanol precipitation, is dissolved in 15 ul TE buffer and stored at −20° C. until needed.

1.3) Cloning of the fbd DNA and production of selected pKSK000 expression plasmids.

The fbd DNA prepared according to 1.2) is inserted into the gene fusion vector pKM2 which has been prepared as described in 1.1). In a typical experiment, 1 ul of SmaI cleaved pKM2 DNA is mixed with 15 ul of target DNA and incubated with 2 U of T4 DNA ligase for 16 hr at 4 C. 1 to 5 ul of the ligation mixture are used to transform 210 ul of a cell suspension of competent E. coli JM109 according to the method of Hanahan (in D. M. Glover, Ed.; DNA Cloning, vol. I, pp. 109–135). After an incubation period of one hour in SOC medium (Hanahan, ibid) aliquote amounts of the culture are spread onto LB agar plates with 100 ug/ml ampicillin and incubated for 16 to 20 hrs at 37° C. The resulting ampicillin resistant colonies have layered upon them a streptokinase assay medium (1% agar, 10% skim milk, 50 mM Tris-HCl, pH 8.1, 150 mM NaCl, 10 ug/ml human plasminogen) and the plates are further incubated at 37° C. (for 2 to 8 hrs) until zones of casein lysis have formed around the colonies. Clones which show a positive streptokinase reaction are purified by single-colony isolation and their plasmid species (termed pKSK expression plasmids) characterized by primary structure analysis. In this manner, the following specific expression plasmids were isolated; pKSK056, pKSK036, pKSK029, pKSK351, pKSK067, and pKSK069.

1.4) Nucleotide sequence analysis of the fused genes.

The DNA fragments which are relevant for the deduction of the primary structure of the trihybrid streptokinases are isolated from the pKSK000 plasmids and cloned into the sequence vectors M13mp18 and M13mp19. In a series of typical additional experiments, the EcoRI-BamHI fragment of the pKSK000 plasmids were isolated, and to give just one example, inserted into mp18 and mp19 and afterwards were sequenced in both directions by the dideoxy-chain termination method according to standard protocol. The nucleotide sequence analysis provides the primary structure for selected gene fusions coding for kringle streptokinases described in the nature of the invention.

1.5) Cultivation of recombinant E. coli JM109(pKSK000) strains and cell lysis.

The recombinant E. coli JM109(pKSK000) strains are cultured under strongly aerobic conditions in LB medium (see above) or 2YT medium (per liter: Bacto= Tryptone, 16 g; Bacto-Yeast Extract, 10 g; NaCl, 5 g, pH 7.5) in the presence of 100 ug of ampicillin and 20 ug/ml isopropyl-beta-D-thiogalactopyranoside until the late logarithmic phase of growth at 37° C. The cells are sedimented by centrifugation and washed in the presence of 40 ug/ml of phenylmethane sulfonylflouride and 50 ug/ml 4-tosylamidol-7-amino-2-heptanon-HCl with Tris buffer (0.1 M Tris, pH 7.4, 1 mM EDTA) or PBS (see above) at 4° C. Subsequently, they are concentrated 10 times in the appropriate buffer solution and lysed with ultrasound or French pressure cell treatment. The cell lysates are clarified by centrifugation (20,000 rpm, 10 minutes), and the supernatant solution is mixed with 0.1 mM thioredoxin and 0.1 mM DTT and kept overnight at 4° C. The resulting preparations serve as the starting material for the analysis and purification of the hybrid streptokinases.

1.6) Isolation of Pg-hybrid streptokinases (kringle-streptokinases) by affinity chromatography.

1.6.1) Preparation of monospecific rabbit antiserum against human plasminogen.

5 mg of purified human plasminogen is dissolved in 0.5 ml NaHCO$_3$ solution (0.1M, pH 8.5) and dialyzed against the same solution. The dialyzed plasminogen is then coupled to Affi-Gel 10 for 4 hours at 4° C., and is then blocked with ethanolamine (1M). After thorough washing of the column with phosphate buffered saline (PBS) and glycine (0.1M; pH 2.7), the column is again equilibrated with PBS and loaded with 4 ml of anti-plasminogen serum. After one hour of reaction time, the column is washed thoroughly with PBS and with distilled water and finally eluted with glycine (0.1M, pH 2.7). Monospecific rabbit antibody fractions, measured in the spectrophotometer at a wavelength of 280 nm, with absorption values >125, were collected after neutralization with Tris-OH (2.5M; pH 10.5), aliquoted into 200 ul fractions and stored at −70° C. 1.6.2) Purification of Kringle streptokinase.

The monospecific rabbit antibody against human plasminogen (as prepared under 1.6.1) is dialyzed against a NaHCO$_3$ solution (0.1M; pH 8.0) and bound to Affi-Gel 10 overnight. After blocking and washing of the gel bed (cf. 1.6.1.) the column is loaded with lysates of E. coli JM109(pKSK000) cells which have been prepared in PBS. They are washed after a reaction time of at least 1 hour (cf 1.6.1) and finally eluted with a glycine solution (0.1M, pH 2.7). The purity of the collected fragments containing kringle streptokinase is determined by comparing the sample material before affinity chromatography by SDS-PAGE and zymography of the gels. As demonstrated by this method, the affinity chromatography removed degradation products without kringle structures and the resulting fusion proteins showed streptokinase activity.

1.7) Lysine binding ©f kringle streptokinase.

Kringle streptokinases which have been purified by immuno-affinity chromatography are dialyzed against a NH$_4$HCO$_3$ solution (0.1M, pH 8.2) and are reacted with Lysine Sepharose overnight at 4° C. with constant agitation of the gel bed. The columns are washed with NH$_4$HCO$_3$ (0.1M, pH 8.2) until the punch-hole plate test for streptokinase activity indicated that the washing fluid was free of streptokinase. Subsequently, the columns are eluted with epsilon-amino caproic acid (EACA; 1M) which has been dissolved in NH$_4$HCO$_3$ solution (0.1M, pH 7.9). The wash and elution fractions and the material before the Lysine-Sepharose chromatography are tested in the punch-hole plate test for streptokinase activity and subjected to SDS-PAGE. The kringle-streptokinase synthesized according to the various steps in Example 1 were subsequently able (with the possible exception of K5-streptokinase) to bind to Lysine Sepharose and could be eluted with EACA.

Example 2

2.1) Production of selected PKSK000T expression plasmids.

The fbd-'skc recombinant pKSK000 expression plasmids pKSK056, pKSK036, pKSK029. pKSK351, pKSK067, and pKSK069 which were obtained following step 1.3) of example 1 are used, on one hand, in the form of a cassette as SstI-SphI fragments and the corresponding fbd-'skc gene fusion, respectively. On the other hand, the aliquote portions of DNA from the *E. coli* expression vector pT7T318U (2.9 kb; selective marker, ampicillin-resistance) are prepared by digestion with restriction enzymes SstI plus SphI for the insertion of the individual fbd-'skc gene cassettes. In a typical experiment, 100 ng of DNA of the pKSK000 expression plasmid are isolated as 2.1 kb (pKSK056), 2.5 kb (pKSK036), 2.1 kb (pKSK029), 2.2 kb (pKSK351), and 3.0 kb (pKSK067 and pKSK069) DNA fragments. They are then purified by phenol extraction and ethanol precipitation. After ligation of the cleaved vector with each of the named fbd-'skc gene fusions, the ligated DNAs are transformed into *E. coli* JM109 selecting for ampicillin resistance as described in step 1.3), are verified for structural integrity of fbd-'skc gene fusions by restriction analysis using the restriction enzymes SstI and PstI, and the *E. coli* strains with the fbd-'skc recombinant expression plasmids pKSK056T, pKSK036T, pKSK029T, pKSK0351, pKSK067, pKSK069 are thus obtained. Each of the *E. coli* JM109(pKSK000T) strains is transformed again according to the protocol of Hanahan (ibid) with 100 ng of plasmid pG1-2, and after double selection of the transformants for resistance to 50 ug/ml kanamycin and ampicillin each, the recombinant *E. coli* JM109(pKSK000T; pGP1-2) strains are obtained.

2.2) Cultivation of the recombinant *E coli* JM109 (PKSK000; pGP1-2) strains for the production of synthetic hybrid streptokinases.

The *E. coli* JM109(pKSK000T; pGP1-2) strains which were obtained according to step 2.1) are incubated at 30° C. under aerobic conditions in a medium consisting of 2% Bacto-Tryptone, 1% Bacto Yeast Extract, 5% NaCl and 0,2% glucose 9Ph7.2) in the presence of ampicillin and kanamycin (50 ug/ml each) up to a cell concentration of $5 \times 10^8$. After reaching the cell density, the cultures are incubated for 25 min at 42° C. for the induction of the T7 polymerase/promoter system. Subsequently, they are mixed with 100 to 200 ug/ml of rifampicin and further incubated for at least two hours at 37° C. After this fermentation regimen has been concluded, cell harvest and cell lysis is performed as described in step 1.5).

Changes may be made in the embodiments of the invention described herein or in parts or elements of the embodiments described herein or in the steps or in the sequence of steps of the methods described herein without departing from the spirit and scope of the invention as defined in the following claims.

What is claimed is:

1. A recombinant DNA molecule comprising sequence comprising the following elements in the 5' to 3' direction, said elements which are operably linked:
   a translation initiation codon;
   four polylinker condons;
   a DNA sequence encoding the first part of a fusion protein, said DNa sequence encoding human plasminogen fibrin binding regions selected from the group consisting of (a) kringle 1, (b) kringle 4, (c) kringle 5, (d) kringle 4 and kringle 5, and (e) kringle 1 and kringle 2 and kringle 3 and kringle 4;
   six polylinker condons; and
   a DNA sequence encoding the second part of a fusion protein, said DNA sequence encoding streptokinase derived from *Streptococcus equisimilis*.

2. The recombinant DNA molecule of claim 1 wherein the DNA sequence encoding human plasminogen fibrin binding regions is derived from one of the following plasmids: pKSK056, pKSK036, pKSK029, pKSK351, and pKSK067.

3. The recombinant DNA molecule of claim 1 wherein the DNA sequence encoding streptokinase is derived from *Streptoccus equisimilis* H46A.

4. A recombinant DNA molecule comprising a sequence comprising the following elements in the 5' to 3' direction, said elements which are operably linked:
   a DNA sequence encoding the first part of a fusion protein, said DNA sequence encoding human plasminogen fibrin binding regions selected from the group consisting of (a) kringle 1, (b) kringle 4, (c) kringle 5, (d) kringle 4 and kringle 5, and (e) kringle 1 and kringle 2 and kringle 3 and kringle 4; and
   a DNA sequence encoding the second part of a fusion protein, said DNA sequence encoding streptokinase derived from *Streptococcus equisimilis*.

5. The recombinant DNA molecule of claim 4 wherein the dNA sequence encoding human plasminogen fibrin binding regions is derived from one of the following plasmids: pKSK056, pKSK036, pKSK029, pKSK351, and pKSK067.

6. The recombinant DNA molecule of claim 4 wherein the DNA sequence encoding streptokinase is derived from Streptococcus equisimilis H46A.

* * * * *

UNITED STATES PATENT AND TRADEMARK OFFICE
CERTIFICATE OF CORRECTION

PATENT NO. : 5,187,098
DATED : February 16, 1993
INVENTOR(S) : Malke, et al.

It is certified that error appears in the above-identified patent and that said Letters Patent is hereby corrected as shown below:

In the Abstract, first line, please delete "of" and substitute --for--.

Column 1, Line 54, in the title, after Kringle, please delete "Streptolinase" and substitute therefore --Streptokinase--.

Column 4, Line 28; after from a, please delete "pq" and substitute therefore --pg--.

Column 4, Line 47, after the, please delete "pKSK" and substitute therefore --pKSK000--.

Col. 5, Line 57, in the title, please delete "PKM" and substitute therefore --pKM--.

UNITED STATES PATENT AND TRADEMARK OFFICE
CERTIFICATE OF CORRECTION

PATENT NO. : 5,187,098

DATED : February 16, 1993

INVENTOR(S) : Malke et al.

It is certified that error appears in the above-identified patent and that said Letters Patent is hereby corrected as shown below:

Column 6, Line 15, in the word streptococcus-pyogenes-, please delete "soeA" and substitute therefore --speA--.

Column 6, Line 18, please delete "soeA" and substitute therefore --speA--.

Column 7, Line 31; in the title, please delete "PKSK000" and substitute therefore --pKSK000--.

Column 7, Line 53; after a2), please delete "PKSK056(K1)" and substitute therefore --pKSK056(K1)--.

UNITED STATES PATENT AND TRADEMARK OFFICE
CERTIFICATE OF CORRECTION

PATENT NO. : 5,187,098

DATED : February 16, 1993

INVENTOR(S) : Malke et al.

It is certified that error appears in the above-identified patent and that said Letters Patent is hereby corrected as shown below:

Column 7, Line 63, after Five, please delete "or" and substitute therefore --of--.

Column 8, Line 4, after kringle, please delete "10" and substitute therefore --1--.

Column 9, Lines 4 & 5; after streptococcus, delete "sanquis" and substitute therefore --sanguis--.

Column 9, Line 21; after The, please delete "PKSK000T" should be --pKSK000T--.

Column 9, Line 43, after SstI, please delete "SohI" and substitute therefore --SphI--.

UNITED STATES PATENT AND TRADEMARK OFFICE
CERTIFICATE OF CORRECTION

PATENT NO. : 5,187,098
DATED : February 16, 1993
INVENTOR(S) : Malke, et al.

It is certified that error appears in the above-identified patent and that said Letters Patent is hereby corrected as shown below:

Column 10, Line 2, after under, please delete "el" and substitute therefore --el--.

Column 10, Line 6, after the, please delete "PKSK000" and substitute therefore --pKSK000--.

Column 10, Line 34, after breviation, please delete "K1 streptokinase" and substitute therefore --K1-streptokinase--.

Column 10, Line 54; after polylinker, please delte "condons" and substitute therefore --codons--.

Column 10, Line 55; after plasminogen-cDNA, please delete "condons" and substitute therefore --codons--.

UNITED STATES PATENT AND TRADEMARK OFFICE
CERTIFICATE OF CORRECTION

PATENT NO. : 5,187,098

DATED : February 16, 1993

INVENTOR(S) : Malke et al.

Page 5 of 8

It is certified that error appears in the above-identified patent and that said Letters Patent is hereby corrected as shown below:

Column 10, Line 56, after linker, please delete "condons" and substitute therefore --codons--.

Column 10, Line 56, after 'skc, please delete "condons" and substitute therefore --codons--.

Column 11, Line 1, after 'skc, please delete "condons" and substitute therefore --codons--.

Column 11, Line 11, after polylinker, please delete "condons" and substitute therefore --codons--.

Column 11, Line 25, after codons;, please delete "420-612" and substiute therefore --41-496--.

Column 11, Line 29, please delete "breviation K1+K2+K3+K4-streptokinase" and substitute therefore --breviation K1+K2+K3+K4-streptokinase--.

UNITED STATES PATENT AND TRADEMARK OFFICE
CERTIFICATE OF CORRECTION

PATENT NO. : 5,187,098

DATED : February 16, 1993

INVENTOR(S) : Malke et al

It is certified that error appears in the above-identified patent and that said Letters Patent is hereby corrected as shown below:

Column 11, Line 58, after Streptococcus, please delete "sanguis" and substitute therefore --sanguis--.

Column 12, Line 26, please delete "strains," and substitute therefore --strains),--.

Column 12, Line 35, please delete "S. sanguis" and substitute therefor --S. sanguis--.

Column 16, Line 32; after 0.5 ml, please delete "$NaHCO_3$" and substitute --$NaHCO_3$--.

UNITED STATES PATENT AND TRADEMARK OFFICE
CERTIFICATE OF CORRECTION

PATENT NO. : 5,187,098

DATED : February 16, 1993

INVENTOR(S) : Malke et al.

It is certified that error appears in the above-identified patent and that said Letters Patent is hereby corrected as shown below:

Column 16, Line 46, please end paragraph with -70°C.

Column 16, Line 46 & 47, please begin paragraph with 1.6.2) Purification

Column 16, Line 64, after binding, please delete "°f" and substitute therefore --of--.

Column 17, Line 51; after opening (, please delete "PKSK000" and substitute therefore --PKSK000T--

UNITED STATES PATENT AND TRADEMARK OFFICE
CERTIFICATE OF CORRECTION

PATENT NO. : 5,187,098
DATED : February 16, 1993
INVENTOR(S) : Malke et al.

It is certified that error appears in the above-identified patent and that said Letters Patent is hereby corrected as shown below:

Column 17, Line 57, after and, please delete "0,2%" and substitute therefore --0.2%--.

Column 17, Line 57, after glucose, please delete "9Ph7.2)" and substitute therefore --pH 7.2--.

Column 18, Line 21, after said, please delete "DNa" and substitute therefore --DNA--.

Column 18, Line 26, after polylinker, please delete "condons" and substitute therefore --codons--.

Column 18, Line 52, after the, please delete "dNA" and substitute therefore --DNA--.

Signed and Sealed this

Eleventh Day of January, 1994

BRUCE LEHMAN

*Attest:*

*Attesting Officer*  *Commissioner of Patents and Trademarks*